United States Patent [19]

Pelosi, Jr.

[11] 4,022,798

[45] May 10, 1977

[54] 2-(5-PHENYL-2-FURYL)IMIDAZOLINES

[75] Inventor: Stanford S. Pelosi, Jr., Norwich, N.Y.

[73] Assignee: Morton-Norwich Products, Inc., Norwich, N.Y.

[22] Filed: May 10, 1976

[21] Appl. No.: 684,723

[52] U.S. Cl. .................. 260/309.6; 260/347.7; 424/273

[51] Int. Cl.$^2$ .................... C07D 405/04

[58] Field of Search ................. 260/309.6

[56] References Cited

UNITED STATES PATENTS

| | | | |
|---|---|---|---|
| 1,999,989 | 4/1935 | Bockmuhl et al. | 260/309.6 |
| 2,457,047 | 12/1948 | Kyrides et al. | 260/309.6 |
| 3,277,112 | 10/1966 | Bencze | 260/309.6 |
| 3,850,926 | 11/1974 | Stahle et al. | 260/309.6 |
| 3,927,023 | 12/1975 | Brown et al. | 260/309.6 |

OTHER PUBLICATIONS

Kelarev et al. Chem. Abst. 1974, vol. 80, No. 37039x.
Kempter et al. Chem. Abst. 1972, vol. 76, No. 99557r.
Schubert et al. Chem. Abst. 1963, vol. 58, cols. 2445–2446.
Tanaseichuk et al. Chem. Abst. 1973, vol. 78, No. 43366b.

*Primary Examiner*—Natalie Trousof
*Attorney, Agent, or Firm*—Anthony J. Franze

[57] ABSTRACT

2-(5-Phenyl-2-furyl)imidazolines are useful as antidepressants.

3 Claims, No Drawings

2-(5-PHENYL-2-FURYL)IMIDAZOLINES

This invention is concerned with 2-(5-phenyl-2-furyl)imidazolines of the formula:

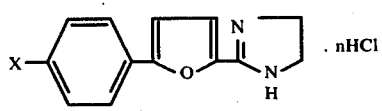

wherein X represents amino or nitro and $n$ is 2 or 1, respectively. These compounds are useful as antidepressants. Their useful antidepressant activity is exhibited in warm blooded animals under the standard ptosisantitetrabenazine test. Thus, when administered perorally in suspension or aqueous solution in a dose of 50 mg/kg to mice shortly prior to intraperitoneal administration of from 1–10 mg/kg of tetrabenazine, ptosis induced by tetrabenazine is curtailed to the extent of from 50–70%.

The method which is currently preferred for the preparation of the compounds of this invention consists in reacting ethyl 5-(4-nitrophenyl)-2-furimidate hydrochloride with ethylenediamine. Catalytic reduction of the nitro compound affords the corresponding amino compound.

In order that this invention may be fully available to and understood by those skilled in the art, the following examples are supplied.

EXAMPLE I

2-[5-(4-Nitrophenyl)-2-furyl]imidazoline Hydrochloride

A mixture of 39 g (0.13 mole) of ethyl 5-(4-nitrophenyl)-2-furimidate hydrochloride and 8.6 g (0.14 mole) of ethylenediamine in 400 ml of absolute ethanol was heated under reflux for 6½ hr and stood in a refrigerator overnight. The yellow solid was collected by filtration and washed with anhydrous ether to give 33 g (85%) of product, m.p. > 300°.

Anal: Calcd. for $C_{13}H_{11}N_3O_3.HCl$: C, 53.16; H, 4.12; N, 14.31. Found: C, 53.34; H, 4.06; N, 14.33.

EXAMPLE II

2-[5-(4-Aminophenyl)-2-furyl]imidazoline Dihydrochloride

A mixture of 33 g (0.11 mole) of the compound of Example I, 1 tsp. of 5% Pd/C, 50% $H_2O$, and 300 ml of methanol was shaken under hydrogen pressure with the theoretical amount of $H_2$ being absorbed. An additional 1400 ml of methanol was added and the reaction mixture was heated to reflux. The catalyst was removed by filtration. The filtrate was cooled to room temperature and ether was added. The solid was filtered and dissolved in refluxing acetic acid. Concentrated hydrochloric acid was added to give a solid which was filtered and dried at 60° to yield 16 g (47%). An analytical sample was prepared by repeating the above procedure a second time and drying in the vacuum pistol at the temperature of refluxing water, m.p. 285°–290°.

Anal: Calcd. for $C_{13}H_{13}N_3O.2HCl$: C, 52.01; H, 5.04; N, 14.00. Found: C, 52.25; H, 5.08; N, 14.03.

What is claimed is:

1. A compound of the formula:

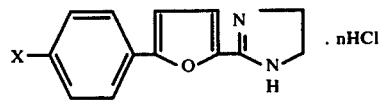

wherein X represents amino or nitro and $n$ is 2 or 1, respectively.

2. The compound 2-[5-(4-nitrophenyl)-2-furyl]imidazoline hydrochloride.

3. The compound 2-[5-(4-aminophenyl)-2-furyl]imidazoline dihydrochloride.

* * * * *